(12) United States Patent
Mikami et al.

(10) Patent No.: US 8,258,174 B2
(45) Date of Patent: Sep. 4, 2012

(54) METHOD OF INHIBITING APOPTOSIS

(75) Inventors: Yoshikazu Mikami, Chiyoda-ku (JP); Masanori Somei, Matsudo (JP)

(73) Assignee: Masanori Somei, Matsudo-shi (JP)

( * ) Notice: Subject to any disclaimer, the term of this patent is extended or adjusted under 35 U.S.C. 154(b) by 0 days.

(21) Appl. No.: 13/059,876

(22) PCT Filed: Aug. 19, 2009

(86) PCT No.: PCT/JP2009/003938
§ 371 (c)(1),
(2), (4) Date: Feb. 18, 2011

(87) PCT Pub. No.: WO2010/021129
PCT Pub. Date: Feb. 25, 2010

(65) Prior Publication Data
US 2011/0306648 A1    Dec. 15, 2011

(30) Foreign Application Priority Data

Aug. 20, 2008  (JP) ................................ 2008-212044

(51) Int. Cl.
*A61K 315/4045* (2006.01)
*A61P 25/28* (2006.01)
*A61P 43/00* (2006.01)

(52) U.S. Cl. ...................................................... 514/415

(58) Field of Classification Search ........................ None
See application file for complete search history.

(56) References Cited

U.S. PATENT DOCUMENTS

| | | | |
|---|---|---|---|
| 6,399,603 | B1 | 6/2002 | Jacobs et al. |
| 2005/0180953 | A1 | 8/2005 | Nebolsin et al. |
| 2005/0261357 | A1 * | 11/2005 | Luu et al. .................... 514/415 |
| 2005/0272761 | A1 | 12/2005 | Graczyk et al. |
| 2006/0004000 | A1 | 1/2006 | D'Orchymont et al. |
| 2009/0005430 | A1 | 1/2009 | Somei et al. |

FOREIGN PATENT DOCUMENTS

| | | |
|---|---|---|
| JP | 8 151366 | 6/1996 |
| JP | 2003 509501 | 3/2003 |
| JP | 2005 532269 | 10/2005 |
| JP | 2005 534618 | 11/2005 |
| JP | 2006 504711 | 2/2006 |
| JP | 3795093 | 4/2006 |
| JP | 3964417 | 6/2007 |

OTHER PUBLICATIONS

Bendheim et al. Development of indole-3-propionic acid (OXIGON) for Alzheimer's disease. Journal of Molecular Neuroscience, Journal of Molecular Neuroscience, vol. 19, 2002.*
Hasegawa et al. Novel formations of 6-mesyloxytryptamines and 1-substituted-3a-(4-chlorobutoxy)-1,2,3,3a,8,8a-hexahydropyrrolo-[2,3-b]indoles in the reaction of Nb-substituted 1-hydroxy-tryptamines with mesyl chloride. Heterocycles, vol. 52, No. 1, 2000.*
Hayashi et al. Nucleophilic substitution reaction on the nitrogen of indole nucleus: a novel synthesis of 1-aryltryptamines. Heterocycles, vol. 57, No. 3, 2002, pp. 421-424.*
International Search Report issued Sep. 29, 2009 in PCT/JP09/03938 filed Aug. 19, 2009.
Boise, H. Lawrence et al., "bcl-x, a bcl-2-Related Gene That Functions as a Dominant Regulator of Apoptotic Cell Death", Cell, vol. 74, pp. 597-608, (Aug. 27, 1993).
Gibson, Leonie et al., "bcl-w, a novel member of the bcl-2 family, promotes cell survival", Oncogene, vol. 13, pp. 665-675, (1996).
Deveraux, L. Quinn et al., "IAP family proteins—suppressors of apoptosis", Genes & Development, vol. 13, pp. 239-252, (1999).

* cited by examiner

*Primary Examiner* — Brandon Fetterolf
*Assistant Examiner* — Anna Pagonakis
(74) *Attorney, Agent, or Firm* — Oblon, Spivak, McClelland, Maier & Neustadt, L.L.P.

(57) ABSTRACT

The invention disclosed is drawn to a method of inhibiting apoptosis comprising administration an effective amount of an indole derivative represented by formula (1) as described herein.

20 Claims, 6 Drawing Sheets

METHOD OF INHIBITING APOPTOSIS

CROSS-REFERENCE TO RELATED APPLICATIONS

This application is a National Stage of PCT/JP09/003,938 filed Aug. 19, 2009 and claims the benefit of JP 2008-212044 filed Aug. 20, 2008.

TECHNICAL FIELD

The present invention relates to an apoptosis inhibitor.

BACKGROUND ART

While apoptosis is a basic life phenomenon, it may cause various diseases and accelerate the progression of the conditions of the diseases. For example, it is known that the apoptosis of nerve cells is responsible for neurodegenerative diseases such as Alzheimer's disease, Parkinson's disease, dementia, Huntington disease, and cerebral ischemia and that apoptosis causes decrease of normal cells (e.g., lymphocytes) which occurs in diseases such as AIDS.

Moreover, the treatment of various diseases may induce apoptosis, resulting in adverse reaction. For example, it is known that cancer therapy using radiation, UV rays, or anticancer agents induces the apoptosis of not only cancer cells but normal cells, resulting in adverse reaction.

Accordingly, if apoptosis is inhibited, the diseases or adverse reaction attributed to cell apoptosis as described above can be prevented or improved. Therefore, a substance inhibiting apoptosis has been developed.

Bcl-2 or the like is known as a protein inhibiting apoptosis, and Bax, Bad, Bak, or the like is known as a gene inducing apoptosis (Non Patent Literatures 1 to 3).

On the other hand, an indole derivative represented by the following formula (1) is known to have α2 receptor blocking effect and vasodilating effect (Patent Literature 1):

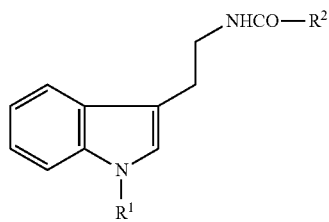

(1)

wherein $R^1$ represents a group selected from a hydrogen atom, an alkyl group having 1 to 6 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an acyl group which may have a substituent, an arylsulfonyl group which may have a substituent, an alkylsulfonyl group having 1 to 6 carbon atoms which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, or a hydroxy group; and $R^2$ represents a group selected from an alkyl group having 1 to 21 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an amino group which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, or a hydroxy group.

Moreover, an indole derivative represented by the formula (1) wherein $R^1$ represents a hydroxy group which may have a substituent; and $R^2$ represents a group selected from an alkyl group having 1 to 21 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, and a hydroxy group which may have a substituent, is known to have antiplatelet aggregation effect (Patent Literature 2).

CITED REFERENCE

Patent Literature

[Patent Literature 1] Japanese Patent No. 3964417
[Patent Literature 2] Japanese Patent No. 3795093
[Non Patent Literature 1] Cell 74, 597-608, 1993
[Non Patent Literature 2] Oncogene 13, 665-675, 1996
[Non Patent Literature 3] Genes Dev. 13, 239-252, 1999

SUMMARY OF INVENTION

Technical Problem

An object of the present invention is to provide a novel apoptosis inhibitor.

Solution to Problem

The present inventors have conducted diligent studies on compounds inhibiting apoptosis and consequently completed the present invention by finding that an indole derivative represented by the following formula (1) has excellent apoptosis inhibitory effect, which is pharmacological effect totally different from a conventionally known one:

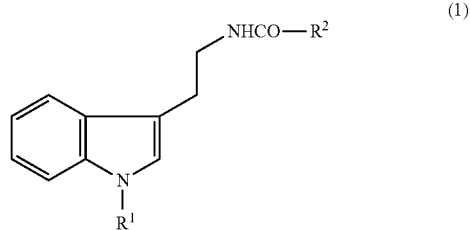

(1)

wherein $R^1$ represents a group selected from a hydrogen atom, an alkyl group having 1 to 6 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an acyl group which may have a substituent, an arylsulfonyl group which may have a substituent, an alkylsulfonyl group having 1 to 6 carbon atoms which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, or a hydroxy group; and $R^2$ represents a group selected from an alkyl group having 1 to 21 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an amino group which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, or a hydroxy group.

Specifically, the present invention provides an apoptosis inhibitor containing an indole derivative represented by the formula (1) or a salt thereof as an active ingredient.

The present invention also provides a pharmaceutical composition for apoptosis inhibition containing an indole derivative represented by the formula (1) or a salt thereof, and a pharmaceutically acceptable carrier.

The present invention also provides use of an indole derivative represented by the formula (1) or a salt thereof for production of an apoptosis inhibitor.

The present invention also provides a method for inhibiting apoptosis, including administering an effective amount of an indole derivative represented by the formula (1) or a salt thereof.

The present invention also provides an indole derivative represented by the formula (1) or a salt thereof for apoptosis inhibition.

Advantageous Effects of Invention

An indole derivative represented by the formula (1) or a salt thereof has apoptosis inhibitory effect. Thus, an apoptosis inhibitor of the present invention is useful as a pharmaceutical or quasi drug for preventing or improving neurodegenerative diseases such as Alzheimer's disease, Parkinson's disease, dementia, Huntington disease, and cerebral ischemia, decrease in normal cells which occurs in diseases such as AIDS, various diseases attributed to cell apoptosis, for example, myocardial infarction, arteriosclerosis, cancer, blood reperfusion injury, and cutaneous vasculitis, and adverse reaction attributed to cell apoptosis, for example, the adverse reaction of cancer therapy using radiation, UV rays or anticancer agents.

BEST MODE FOR CARRYING OUT THE INVENTION

Figure 1:
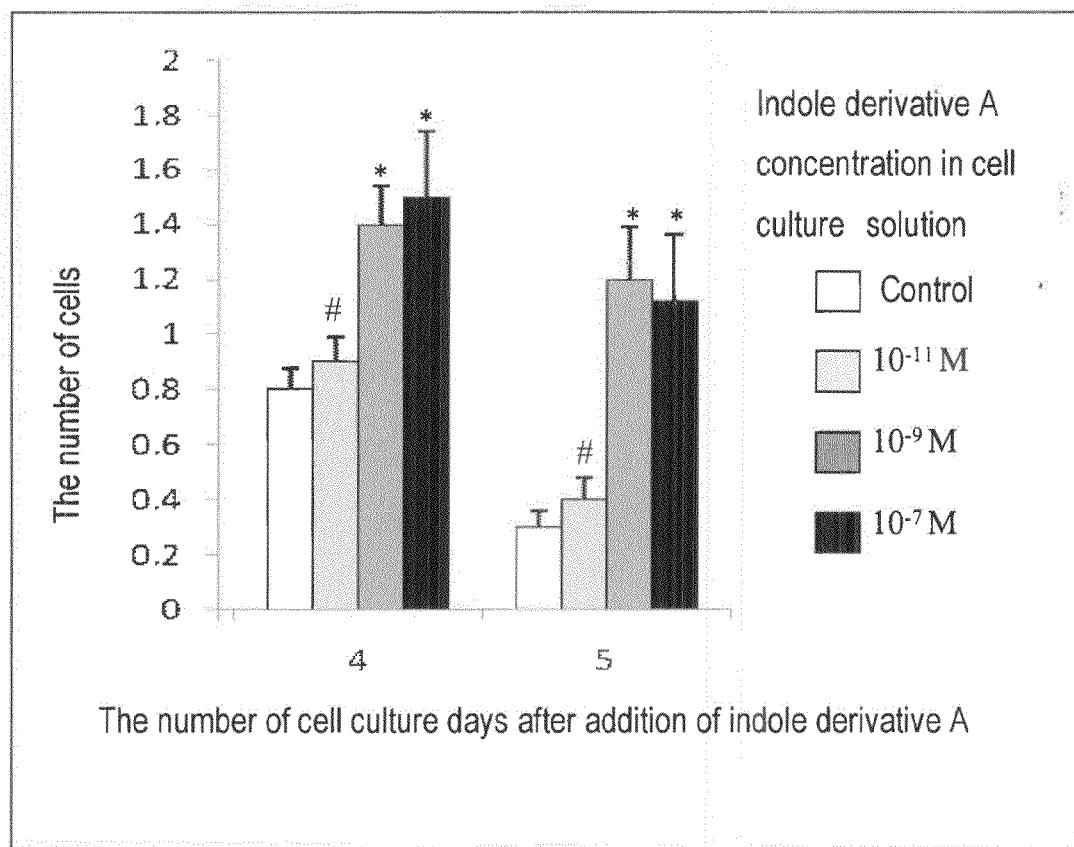
FIG. 1 is a diagram showing the influence of an indole derivative A on apoptosis.

An active ingredient in an apoptosis inhibitor of the present invention is an indole derivative represented by the formula (1).

In the formula (1), examples of the alkyl group having 1 to 6 carbon atoms represented by $R^1$ include linear, branched, or cyclic alkyl groups, such as methyl, ethyl, propyl, isopropyl, butyl, isobutyl, sec-butyl, tert-butyl, pentyl, isopentyl, hexyl, cyclopropyl, cyclobutyl, cyclopentyl, and cyclohexyl groups.

In the formula (1), examples of the alkenyl group having 2 to 6 carbon atoms represented by $R^1$ include vinyl, 1-propenyl, allyl, 1-butenyl, 2-butenyl, pentenyl, and hexenyl groups.

In the formula (1), examples of the alkynyl group having 2 to 6 carbon atoms represented by $R^1$ include ethynyl, 1-propynyl, 2-propynyl (propargyl), 3-butynyl, pentynyl, and hexynyl groups.

In the formula (1), the aromatic group represented by $R^1$ is preferably an aromatic group having 6 to 14 carbon atoms. Examples thereof include: aromatic hydrocarbon groups such as phenyl, tolyl, and naphthyl groups; and aromatic heterocyclic groups such as furyl, thienyl, pyrrolyl, oxazolyl, isoxazolyl, thiazolyl, isothiazolyl, imidazolyl, pyrazolyl, pyridyl, pyrimidinyl, pyridazinyl, pyrazinyl, quinolyl, and isoquinolyl groups.

In the formula (1), the aralkyl group represented by $R^1$ is preferably an aralkyl group having 7 to 20 carbon atoms in total. Examples thereof include benzyl and phenethyl groups.

In the formula (1), examples of the acyl group represented by $R^1$ include: aliphatic acyl groups having 1 to 6 carbon atoms such as formyl, acetyl, propionyl (propanoyl), butyryl (butanoyl), valeryl (pentanoyl), and hexanoyl groups; and aromatic acyl groups (aroyl groups) having 7 to 15 carbon atoms in total such as benzoyl and toluoyl groups.

In the formula (1), the arylsulfonyl group represented by $R^1$ is preferably an arylsulfonyl group having 6 to 14 carbon atoms. Examples thereof include: aromatic hydrocarbon-sulfonyl groups such as phenylsulfonyl (benzenesulfonyl), p-toluenesulfonyl (tosyl), and naphthalenesulfonyl groups; and aromatic heterocycle-sulfonyl groups such as furansulfonyl, thiophenesulfonyl, pyrrolesulfonyl, oxazolesulfonyl, isoxazolesulfonyl, thiazolesulfonyl, isothiazolesulfonyl, imidazolesulfonyl, pyrazolesulfonyl, pyridinesulfonyl, pyrimidinesulfonyl, pyridazinesulfonyl, pyrazinesulfonyl, quinolinesulfonyl, and isoquinolinesulfonyl groups.

In the formula (1), examples of the alkylsulfonyl group having 1 to 6 carbon atoms represented by $R^1$ include methanesulfonyl (mesyl) and ethanesulfonyl groups.

In the formula (1), examples of the alkoxy group having 1 to 6 carbon atoms represented by $R^1$ include methoxy, ethoxy, propoxy, isopropoxy, butoxy, isobutoxy, sec-butoxy, tert-butoxy, pentyloxy, isopentyloxy, hexyloxy, cyclopropyloxy, cyclobutyloxy, cyclopentyloxy, and cyclohexyloxy groups.

In the formula (1), examples of the alkenyloxy group having 2 to 6 carbon atoms represented by $R^1$ include vinyloxy, 1-propenyloxy, allyloxy, 1-butenyloxy, 2-butenyloxy, pentenyloxy, and hexenyloxy groups.

In the formula (1), examples of the alkynyloxy group having 2 to 6 carbon atoms represented by $R^1$ include ethynyloxy, 1-propynyloxy, and propargyloxy groups.

In the formula (1), examples of the aryloxy group represented by $R^1$ include: aromatic hydrocarbon-oxy groups such as phenoxy and naphthyloxy groups; and aromatic heterocycle-oxy groups such as furyloxy, thienyloxy, pyrrolyloxy, oxazolyloxy, isoxazolyloxy, thiazolyloxy, isothiazolyloxy, imidazolyloxy, pyrazolyloxy, pyridyloxy, pyrimidinyloxy, pyridazinyloxy, pyrazinyloxy, quinolyloxy, and isoquinolyloxy groups.

In the formula (1), examples of the aralkyloxy group represented by $R^1$ include benzyloxy and phenethyloxy groups.

In the formula (1), examples of the acyloxy group represented by $R^1$ include: $C_{1-6}$ aliphatic acyloxy groups such as formyloxy, acetyloxy, propanoyloxy, butanoyloxy, pentanoyloxy, and hexanoyloxy groups; and aroyloxy groups such as benzoyloxy and toluoyloxy groups.

In the formula (1), examples of the alkyl group having 1 to 21 carbon atoms represented by $R^2$ include linear, branched, or cyclic alkyl groups, such as methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, cyclopropyl, cyclobutyl, cyclopentyl, and cyclohexyl groups. Alkyl groups having 1 to 9 carbon atoms are preferable in terms of apoptosis inhibitory effect.

In the formula (1), the alkenyl group having 2 to 6 carbon atoms, the alkynyl group having 2 to 6 carbon atoms, the aromatic group, the aralkyl group, the alkoxy group having 1 to 6 carbon atoms, the alkenyloxy group having 2 to 6 carbon atoms, the alkynyloxy group having 2 to 6 carbon atoms, the aryloxy group, and the aralkyloxy group, and the acyloxy group, represented by $R^2$, are the same as those exemplified in $R^1$.

Moreover, in the present invention, examples of substituents include one or more substituents selected from the same aromatic group as above, the same alkyl group having 1 to 6 carbon atoms as above, the same alkenyl group having 2 to 6 carbon atoms as above, the same alkynyl group having 2 to 6 carbon atoms as above, the same acyl group as above, the same aralkyl group as above, an amino group, a hydroxy group, a carboxyl group, a halogen atom, and the same alkoxy group having 1 to 6 carbon atoms as above.

Of these substituents, a substituent by which the alkyl group having 1 to 6 carbon atoms, the alkenyl group having 2 to 6 carbon atoms, the alkynyl group having 2 to 6 carbon atoms, and the alkylsulfonyl group having 1 to 6 carbon atoms represented by $R^1$ and the alkyl group having 1 to 21 carbon atoms, the alkenyl group having 2 to 6 carbon atoms, the alkynyl group having 2 to 6 carbon atoms, the aromatic group, the aralkyl group, and the alkoxy group represented by $R^2$ may be substituted preferably includes one or more substituents selected from the aromatic group, the acyl group, the hydroxy group, the carboxyl group, the amino group, the halogen atom, and the alkoxy group having 1 to 6 carbon atoms.

Moreover, of these substituents, a substituent by which the aromatic group, the aralkyl group, the acyl group, and the arylsulfonyl group represented by $R^1$ may be substituted preferably includes one or more substituents selected from the alkyl group having 1 to 6 carbon atoms, the alkenyl group having 2 to 6 carbon atoms, the alkynyl group having 2 to 6 carbon atoms, the hydroxy group, the carboxyl group, the halogen atom, and the alkoxy group having 1 to 6 carbon atoms.

Moreover, of these substituents, a substituent by which the amino group represented by $R^2$ may be substituted preferably includes one or more substituents selected from the alkyl group having 1 to 6 carbon atoms, the alkenyl group having 2 to 6 carbon atoms, the alkynyl group having 2 to 6 carbon atoms, the aromatic hydrocarbon group, the aromatic heterocyclic group, the aralkyl group, and the acyl group.

Moreover, in the present invention, $R^1$ is preferably a hydrogen atom or a hydroxy group, and more preferably a hydrogen atom, and $R^2$ is preferably an octyl group or a methoxy group, and more preferably an octyl group.

Specifically, in the present invention, the indole derivative represented by the formula (1) is preferably 1-hydroxy-N-methoxycarbonyltryptamine or N-nonanoyltryptamine, and particularly preferably N-nonanoyltryptamine, in terms of apoptosis inhibitory effect.

The salt of the indole derivative represented by the formula (1) can be any pharmaceutically acceptable salt. Examples thereof include: inorganic acid salts such as hydrochloride, sulfate, phosphate, hydrobromide, hydroiodide, nitrate, pyrosulfate, and metaphosphate; and organic acid salts such as citrate, benzoate, acetate, propionate, fumarate, maleate, and sulfonate (e.g., methanesulfonate, p-toluenesulfonate, and naphthalenesulfonate). Moreover, when the indole derivative represented by the formula (1) has a phenolic hydroxy or carboxyl group, the salt thereof may be an alkali metal salt such as sodium or potassium salt.

The indole derivative represented by the formula (1) of the present invention can be obtained by, for example, methods described in Patent Literatures 1 and 2.

The indole derivative represented by the formula (1) and the salt thereof have excellent apoptosis inhibitory effect, as shown in Examples described later.

Thus, an apoptosis inhibitor containing the indole derivative represented by the formula (1) or the salt thereof as an active ingredient is useful as a pharmaceutical or quasi drug for preventing or improving neurodegenerative diseases such as Alzheimer's disease, Parkinson's disease, dementia, Huntington disease, and cerebral ischemia, decrease in normal cells which occurs in diseases such as AIDS, various diseases attributed to cell apoptosis such as myocardial infarction, arteriosclerosis, cancer, blood reperfusion injury, and cutaneous vasculitis, and adverse reaction attributed to cell apoptosis such as the adverse reaction of cancer therapy using radiation, UV rays or anticancer agents.

The apoptosis inhibitor of the present invention, when used as a pharmaceutical or quasi drug, can be administered in an arbitrary dosage form. Examples of the dosage form include: oral agents such as tablets, capsules, granules, sugar-coated tablets, pills, subtle granules, powders, dusts, sustained-release formulations, suspensions, emulsions, syrups, liquid formulations, and elixirs; and parenteral agents such as injections for intravenous, intramuscular, hypodermic, or dripping injection, formulations for external use such as liniments and patches, suppositories, infusion solutions, and percutaneous, transmucosal, nasal, inhalant, or porous formulations.

Moreover, the formulation used as a pharmaceutical or quasi drug can be produced by a routine method. The indole derivative represented by the formula (1) of the present invention or the salt thereof may be used alone or in combination with a pharmaceutically acceptable carrier. Examples of the pharmaceutically acceptable carrier include excipients, binders, disintegrants, surfactants, lubricants, flow promoters, taste corrigents, coloring agents, flavors, diluents, germicides, osmotic adjusters, pH adjusters, emulsifiers, antiseptics, stabilizers, absorption aids, antioxidants, UV absorbers, humectants, thickeners, brighteners, activity enhancers, antiinflammatory agents, tonicity agents, soothing agents, and odor corrigents.

Examples of the binders include starch, dextrin, gum arabic, gelatin, hydroxypropyl starch, methylcellulose, carboxymethylcellulose sodium, hydroxypropylcellulose, crystalline cellulose, ethylcellulose, polyvinylpyrrolidone, and macrogol.

Examples of the disintegrants include starch, hydroxypropyl starch, carboxymethylcellulose sodium, carboxymethylcellulose calcium, carboxymethylcellulose, and low-substituted hydroxypropylcellulose.

Examples of the surfactants include sodium lauryl sulfate, soybean lecithin, sucrose fatty acid ester, and polysorbate 80.

Examples of the lubricants include talc, waxes, hydrogenated plant oil, sucrose fatty acid ester, magnesium stearate, calcium stearate, aluminum stearate, and polyethylene glycol.

Examples of the flow promoters include light anhydrous silicic acid, dry aluminum hydroxide gel, synthetic aluminum silicate, and magnesium silicate.

Examples of the diluents include injectable diluted water, saline, an aqueous glucose solution, olive oil, sesame oil, peanut oil, soybean oil, corn oil, propylene glycol, and polyethylene glycol.

Moreover, specific examples of preferable production methods of oral agents as a dosage form include a method that performed according to a routine method by using starch, lactose, saccharose, mannitol, carboxymethylcellulose, corn starch, inorganic salts, and so on. Specific examples of preferable production methods of injections as a dosage form include a method which involves combining diluents, adding a germicide, an antiseptic, and a stabilizer, freezing the mixture after charging into a vial or the like, removing water therefrom by a usual freeze-dry technique, and repreparing a liquid formulation by using the freeze-dried product immediately before use.

The content of the indole derivative represented by the formula (1) of the present invention or the salt thereof in the formulation is preferably 0.1 to 100% by mass.

Moreover, when the apoptosis inhibitor of the present invention is used as an oral agent, its daily dose in one adult may be, for example, 1 to 200 mg in terms of the amount of the indole derivative represented by the formula (1) or the salt thereof, which is appropriately taken in several portions per day, although the dose differs depending on the age, body weight, and severity of the patient.

Moreover, when the apoptosis inhibitor of the present invention is used as a parenteral agent, its daily dose in one adult may be, for example, 1 to 50 mg in terms of the amount of the indole derivative represented by the formula (1) or the salt thereof, although the dose differs depending on the age, body weight, and severity of the patient.

EXAMPLES

Hereinafter, the present invention will be described more specifically with reference to Examples. However, the present invention is not limited to them by any means.
1) Preparation of Indole Derivative
In this test, N-nonanoyltryptamine (in the diagrams, referred to as an indole derivative A) and 1-hydroxy-N-methoxycarbonyltryptamine (in the diagrams, referred to as an indole derivative B) were used.

Synthesis methods thereof followed methods described in Patent Literatures 1 and 2.

Each synthesized compound was dissolved at a concentration of $10^{-2}$ M in dimethyl sulfoxide to prepare a stock solution, and the solution was then added to a cell culture solution to final concentration of $10^{-7}$ M to $10^{-11}$ M. Moreover, only dimethyl sulfoxide was added to an indole derivative-free culture system (in the diagrams, referred to as a control).
2) Cell and Culture In this test, a rat osteosarcoma-derived cultured cell strain ROS17/2.8 was used. The cells were cultured in α-MEM (Wako Pure Chemical Industries, Ltd.) containing 10% FBS (JRH Biosciences), 100 U/ml penicillin (GIBCO), and 100 μg/ml streptomycin (GIBCO). The cell culture was performed under conditions of 37° C. and 5% $CO_2$ according to a routine method. The medium was replaced every two days until the cells became confluent.
3) Measurement of the Number of Cells The cells were inoculated at a cell density of 1200 cells/well to a 96-well plate and precultured under the conditions described above (the amount of the medium: 100 μl/well) until confluent. Then, the cells were cultured for 1 day to 5 days under indole derivative-supplemented (concentration in the medium: described in the diagrams) or -free conditions.

After the confluence, culture was performed without medium replacement to induce apoptosis.

After the culture, water-soluble tetrazolium salt* (DOJINDO LABORATORIES; Cell Counting Kit-8) was added at a concentration of 10 μl/well, and color reaction was performed for 1 hour under conditions of 37° C. and 5% $CO_2$. Then, absorbance at 450 nm was measured using a microplate reader.

*: water-soluble tetrazolium salt is reduced by intracellular dehydrogenase to form water-soluble formazan having the maximum absorption around 460 nm. Therefore, the amount of formazan dye produced according to intracellular dehydrogenase activity is proportional to the number of living cells.
4) Observation of Cell The cells were observed using an Olympus optical microscope (A×80) and photographed using an Olympus digital camera (CAMDIA C-4040 ZOOM).
5) Measurement of mRNA Expression Level by Using Real-Time RT-PCR
RNA Extraction Cells cultured in a 6-well plate until confluent were further cultured for 48 hours under indole derivative-supplemented (concentration in the medium: described in the diagrams) or -free conditions.

After the culture, the medium was removed, and 1 ml of TRIzol (Invitrogen Corp.) was added to the cells and stirred. The solution was transferred to a 1.5-ml tube. 200 μl of chloroform was added thereto, and the mixture was vigorously stirred for 30 seconds and centrifuged at 15000 rpm for 15 minutes. 400 μl of the supernatant was transferred to a new tube, and 400 μl of isopropanol was added thereto. The tube was shaken and then left at room temperature for 5 minutes. After centrifugation at 15000 rpm for 15 minutes, the supernatant was discarded, and the precipitate was washed with 1 ml of 70% ethanol. After removal of ethanol, the residue (total RNA) was dissolved by addition of 50 μl of sterilized distilled water.
cDNA Synthesis 200 μg of random primers and 2.5 mM each dNTP mix were added to 2 μg of total RNA, and the mixture was adjusted to 12 μl of the total amount with sterilized distilled water. The solution was heated at 60° C. for 10 minutes and then cooled on ice. 4 μl of 5× First strand buffer (Invitrogen Corp.), 2 μl of 0.1 M DTT, and 1 μl of RNase OUT (Invitrogen Corp.) were added thereto, and the mixture was stirred and then left at room temperature for 2 minutes. 1 μl of Reverse transcriptase (Invitrogen Corp.) was added thereto, and the mixture was incubated at 25° C. for 10 minutes, at 42° C. for 50 minutes, and at 70° C. for 15 minutes.

Real-time-RT-PCR

The synthesized cDNA was used as a template to prepare the following reagent:

| | |
|---|---|
| cDNA | 0.1 μl |
| Forward primer (10 μM) | 0.5 μl |
| Reverse primer (10 μM) | 0.5 μl |
| SYBER Premix EX Taq (TAKARA BIO INC.) | 12.5 μl |
| H$_2$O | 10.5 μl |
| Total | 25 μl |

Two-step PCR was performed at a cycle involving 95° C. for 3 seconds and 60° C. for 20 seconds using Smart Cycler II System (TAKARA BIO INC.). The relative expression level of the target gene was calculated using the expression level of GAPDH as an internal standard gene. Primer sequences used in real-time RT-PCR are shown below.

```
                                            (SEQ ID NO: 1)
Bcl-2 Fw 5'-TGTCCAGTCAGCTGCA-3'

(SEQ ID NO: 2)
Bcl-2 Rv 5'-TGACCCCACCGAACTCA-3'

(SEQ ID NO: 3)
Bax Fw 5'-GGGTGGCAGCTGACATGTTT-3'

(SEQ ID NO: 4)
Bax Rv 5'-CGCTCACGGAGGAAGTCCAG-3'

(SEQ ID NO: 5)
Bad Fw 5'-CTCGCTGGCTCCTGCACACG-3'

(SEQ ID NO: 6)
Bad Rv 5'-GCGTCTTCCTGCTCACTCGG-3'

(SEQ ID NO: 7)
Bak Fw 5'-GCTTCAGCCCACCGCTGGGA-3'

(SEQ ID NO: 8)
Bak Rv 5'-CACGCTGGTAGACATACAGG-3'

(SEQ ID NO: 9)
GAPDH Fw 5'-GTGAAGGTCGGTGTGAACGG-3'

(SEQ ID NO: 10)
GAPDH Rv 5'-GAGTCATACTGGAACATGTAG-3'
```

Data Analysis

In this test, standard deviation was calculated by using results of three experiments. Moreover, significant difference test based on Student's t-test was conducted in data comparison with each control experiment. When the p value is lower than 0.05, significant difference was confirmed and indicated by using * in the diagrams. When the p value is equal to or higher than 0.05, the results were indicated by using # in the diagrams.

6) Results

Figure 2:
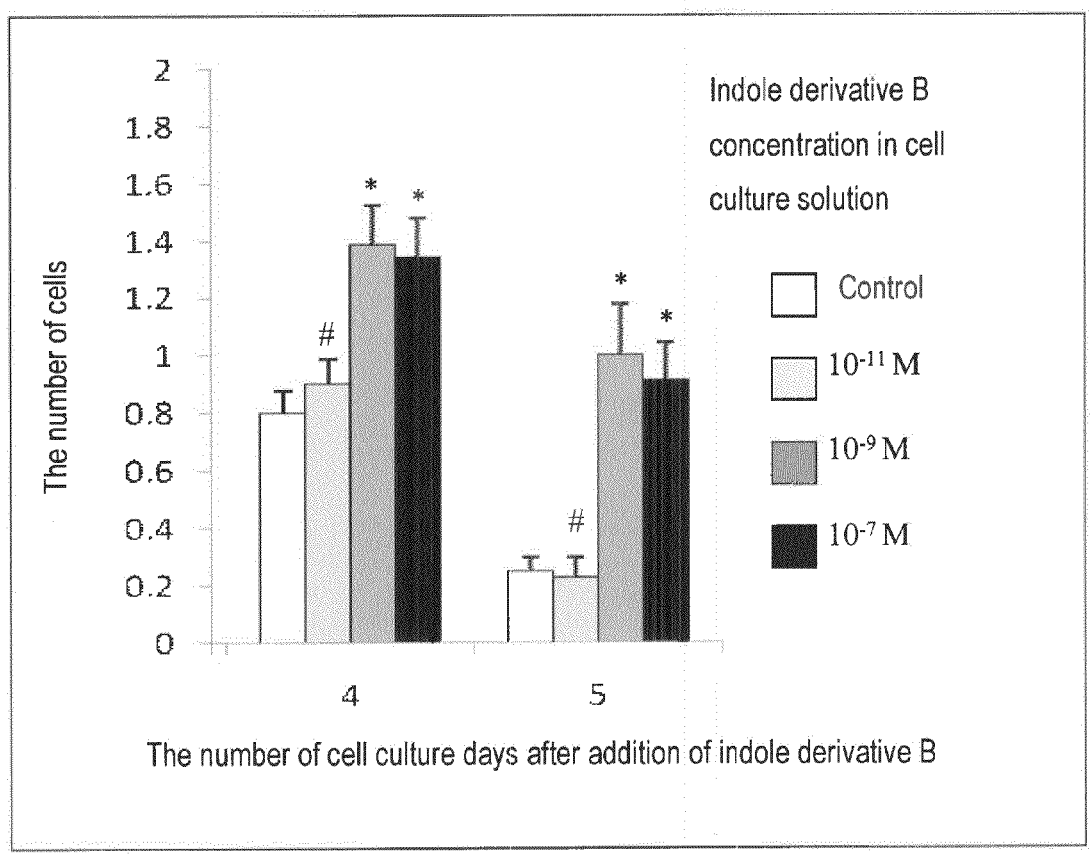
FIG. 2 is a diagram showing the influence of an indole derivative B on apoptosis.
Figure 3:
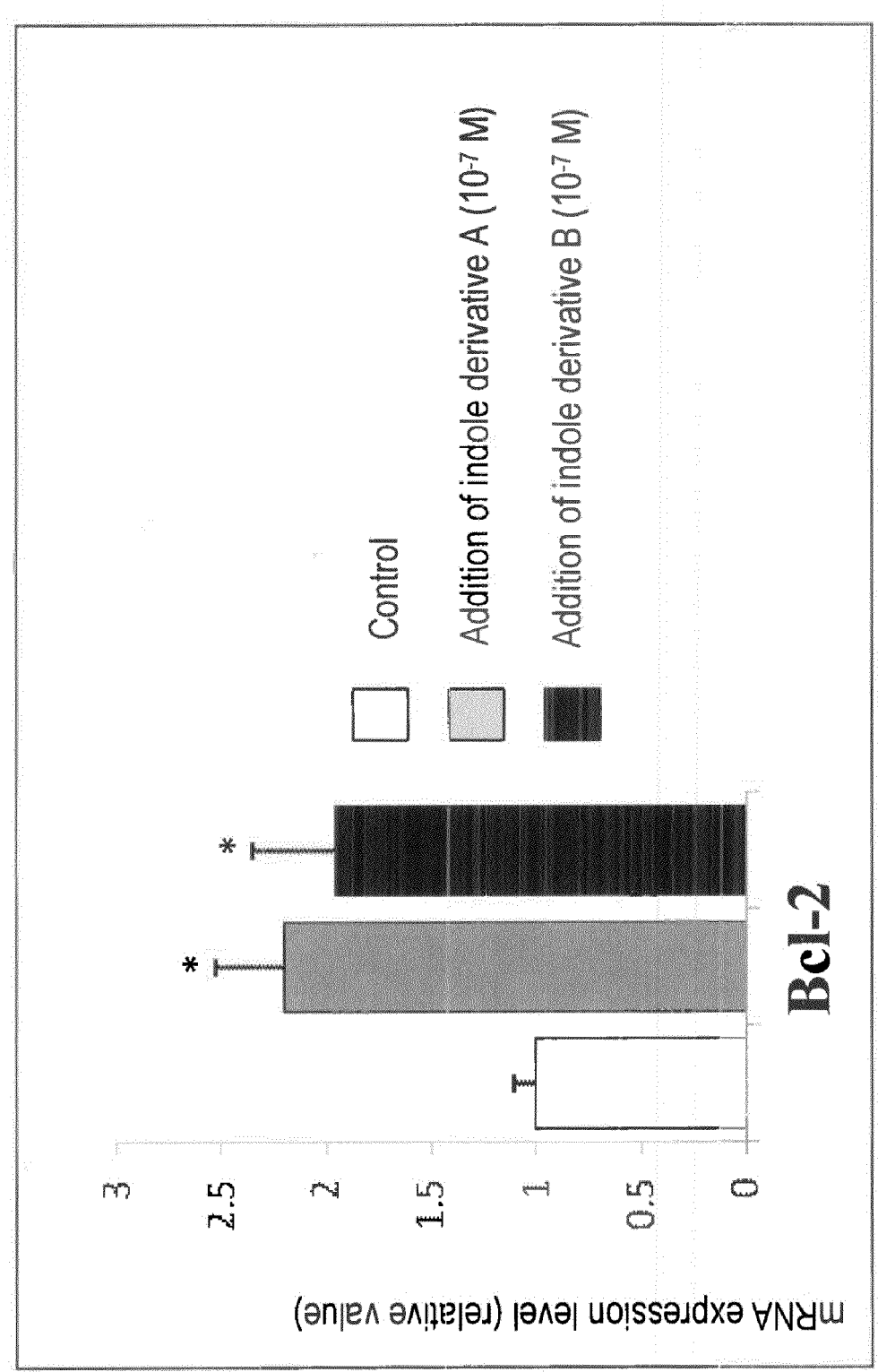
FIG. 3 is a diagram showing the influence of the indole derivative on the expression level of an apoptosis-inhibiting gene.
Figure 4:
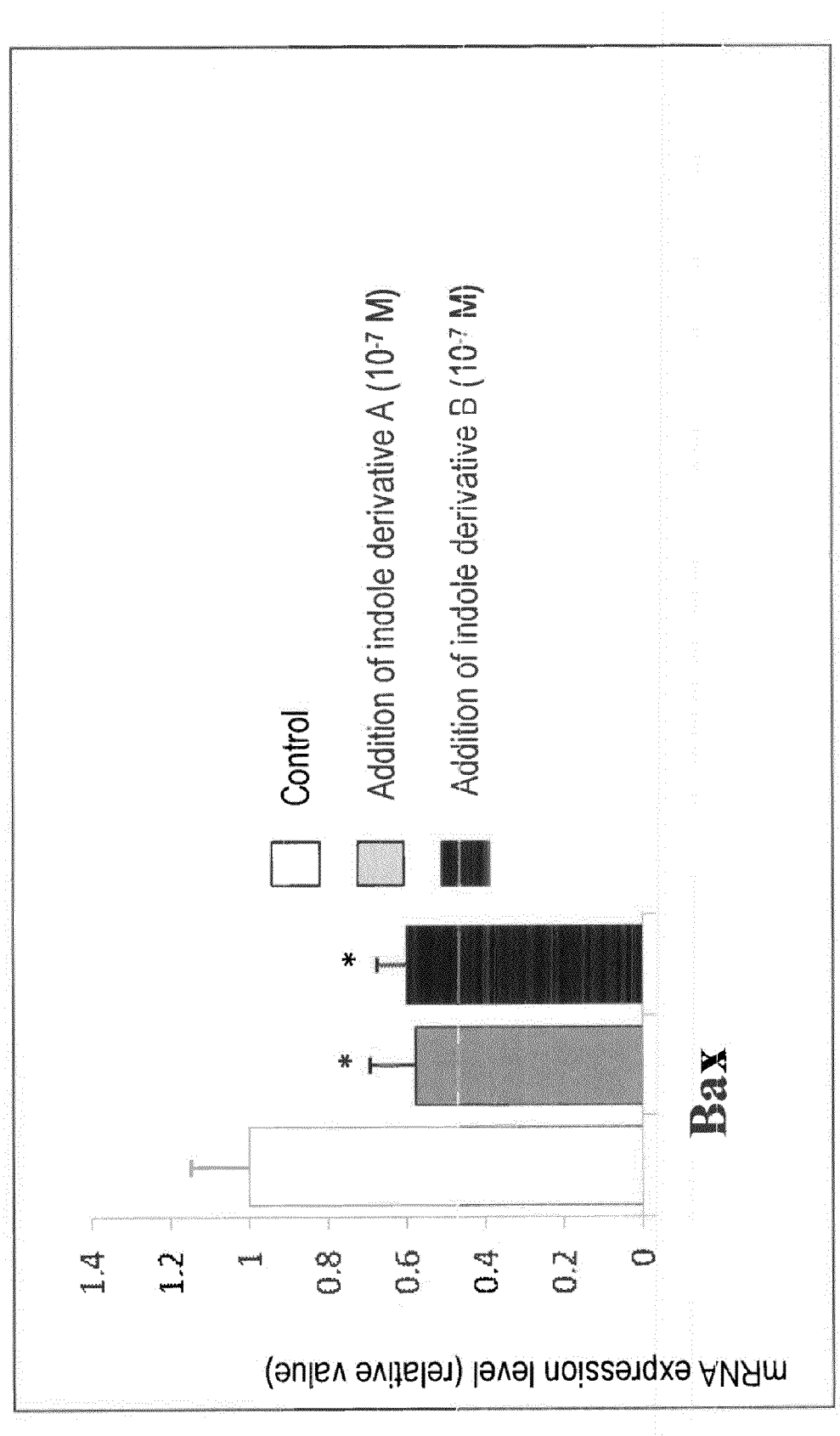
FIG. 4 is a diagram showing the influence of the indole derivative on the expression level of an apoptosis-inducing gene.
Figure 5:
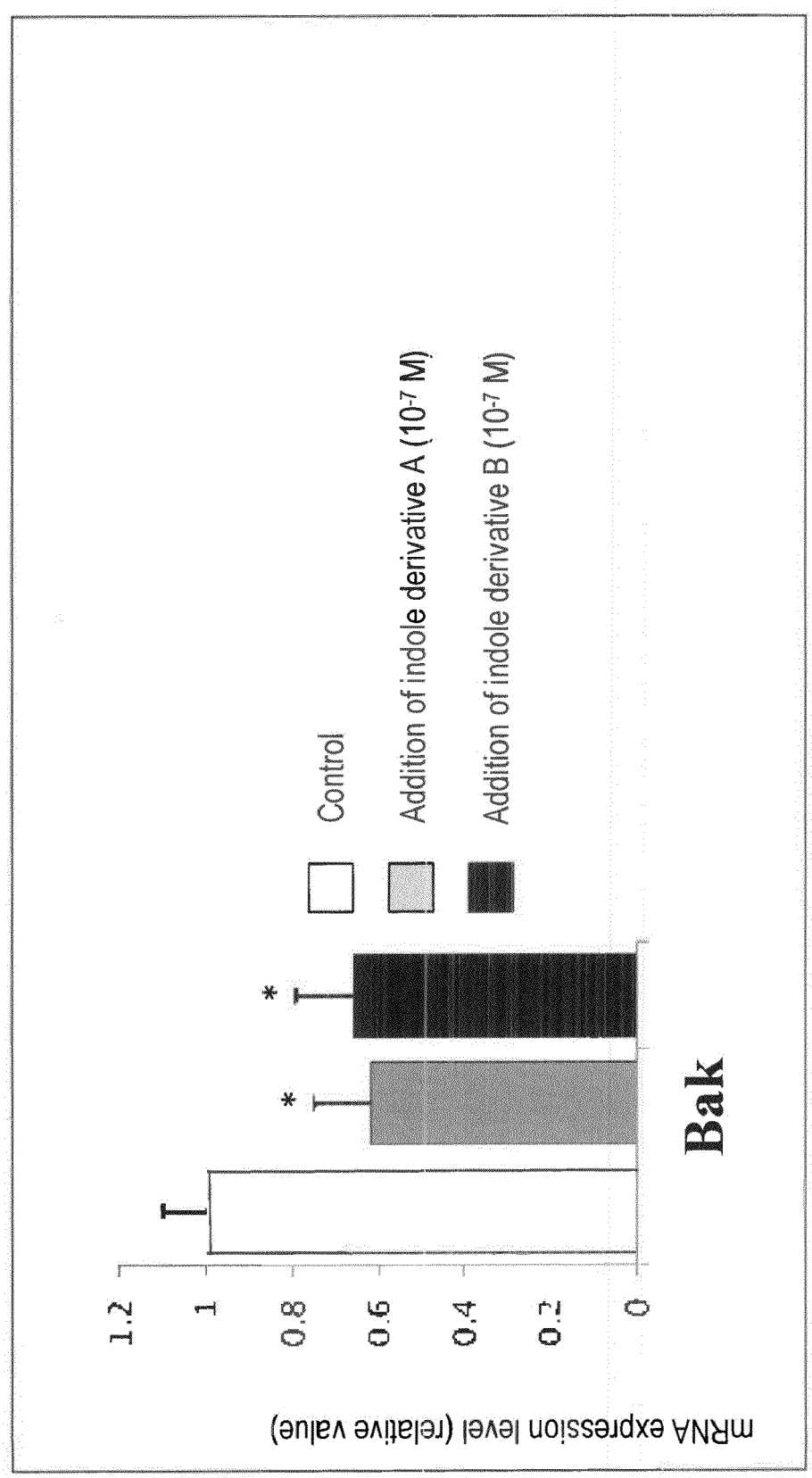
FIG. 5 is a diagram showing the influence of the indole derivative on the expression level of an apoptosis-inducing gene.
Figure 6:
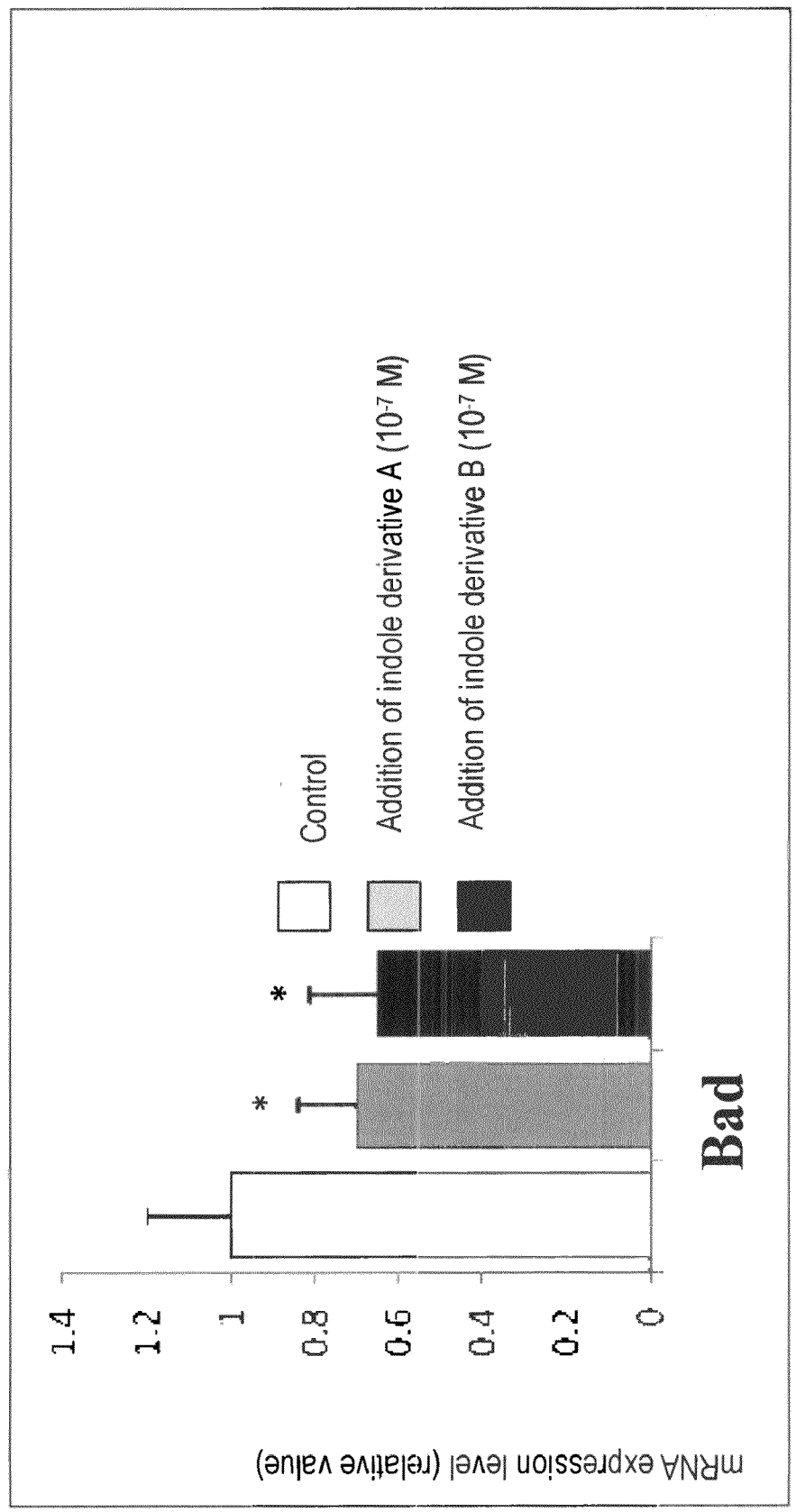
FIG. 6 is a diagram showing the influence of the indole derivative on the expression level of an apoptosis-inducing gene.

The influence of each indole derivative on apoptosis is shown in FIGS. 1 and 2.

Decrease in the number of living cells was significantly inhibited on culture day 4 to 5 in cells cultured in a well supplemented with each indole derivative at a concentration of $10^{-7}$ M or $10^{-9}$ M, compared with that in cells cultured in an indole derivative-free well. This indicates that the effect of the indole derivative inhibited the induction of apoptosis due to starvation.

The influence of each indole derivative on the expression levels of an apoptosis-inhibiting gene and an apoptosis-inducing gene is shown in FIGS. 3 to 6. The mRNA expression level of the apoptosis-inhibiting gene Bcl-2 was increased in cells cultured in a well supplemented with each indole derivative at a concentration of $10^{-7}$ M, compared with that in cells cultured in an indole derivative-free well, whereas the mRNA expression levels of the apoptosis-inducing genes Bax, Bak, and Bad were decreased therein.

These results indicate that the indole derivative is effective for apoptosis inhibition. Furthermore, this apoptosis inhibitory effect of the indole derivative is probably based on the induction of Bcl-2 mRNA expression and the inhibition of Bax, Bak, and Bad mRNA expression levels.

Specifically, the indole derivative is useful as an apoptosis inhibitor and useful against neurodegenerative diseases such as Alzheimer's disease, Parkinson's disease, dementia, Huntington disease, and cerebral ischemia, decrease in normal cells which occurs in diseases such as AIDS, various diseases attributed to cell apoptosis such as myocardial infarction, arteriosclerosis, cancer, blood reperfusion injury, and cutaneous vasculitis, and adverse reaction attributed to cell apoptosis such as the adverse reaction of cancer therapy using radiation, UV rays or anticancer agents.

The invention claimed is:

1. A method for inhibiting apoptosis, comprising:
   administering an effective amount of an indole derivative represented by formula (1) or a salt thereof to a subject in need thereof

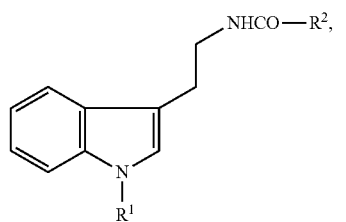

(1)

wherein $R^1$ represents a group selected from the group consisting of a hydrogen atom, an alkyl group having 1 to 6 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an acyl group which may have a substituent, an arylsulfonyl group which may have a substituent, an alkylsulfonyl group having 1 to 6 carbon atoms which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, and a hydroxyl group, and $R^2$ represents a group selected from the group consisting of an alkyl group having 1 to 21 carbon atoms, an alkenyl group having 2 to 6 carbon atoms which may have a substituent, an alkynyl group having 2 to 6 carbon atoms which may have a substituent, an aralkyl group which may have a substituent, an amino group which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, an acyloxy group which may have a substituent, and a hydroxyl group.

2. The method of claim 1, wherein
$R^1$ represents a group selected from the group consisting of a hydrogen atom, an alkyl group having 1 to 6 carbon atoms which may have a substituent, an alkenyl group having 2 to 6 carbon atoms which may have a substituent, an alkynyl group having 2 to 6 carbon atoms which may have a substituent, an aromatic group which may have a substituent, an aralkyl group which may have a substituent, an alkoxy group having 1 to 6 carbon atoms which may have a substituent, an alkenyloxy group having 2 to 6 carbon atoms which may have a substituent, an alkynyloxy group having 2 to 6 carbon atoms which may have a substituent, an aryloxy group which may have a substituent, an aralkyloxy group which may have a substituent, and a hydroxyl group, and $R^2$ represents an alkyl group having 1 to 21 carbon atoms or an alkoxy group having 1 to 6 carbon atoms which may have a substituent.

3. The method of claim 1, wherein
$R^1$ represents a hydrogen atom or a hydroxyl group, and
$R^2$ represents an alkyl group having 1 to 21 carbon atoms or an alkoxy group having 1 to 6 carbon atoms which may have a substituent.

4. The method of claim 1, wherein
R$^1$ represents a hydrogen atom or a hydroxyl group, and
R$^2$ represents an octyl group or a methoxy group.

5. The method of claim 1, wherein the indole derivative is 1-hydroxy-N-methoxycarbonyltryptamine or N-nonanoyl-tryptamine.

6. The method of claim 1, wherein R$^2$ represents an alkyl group having 1 to 21 carbon atoms.

7. The method of claim 1, wherein R$^2$ represents an alkoxy group having 1 to 6 carbon atoms which may have a substituent.

8. The method of claim 1, wherein R$^2$ represents an octyl group.

9. The method of claim 1, wherein R$^2$ represents a methoxy group.

10. The method of claim 6, wherein R$^1$ represents a hydrogen atom.

11. The method of claim 7, wherein R$^1$ represents a hydrogen atom.

12. The method of claim 8, wherein R$^1$ represents a hydrogen atom.

13. The method of claim 9, wherein R$^1$ represents a hydrogen atom.

14. The method of claim 6, wherein R$^1$ represents a hydroxyl group.

15. The method of claim 7, wherein R$^1$ represents a hydroxyl group.

16. The method of claim 8, wherein R$^1$ represents a hydroxyl group.

17. The method of claim 9, wherein R$^1$ represents a hydroxyl group.

18. The method of claim 1, wherein the indole derivative is 1-hydroxy-N-methoxycarbonyltryptamine.

19. The method of claim 1, wherein the subject in need thereof has Alzheimer's disease.

20. The method of claim 19, wherein the subject in need thereof has Alzheimer's disease.

* * * * *

SEQUENCE LISTING

```
<160> NUMBER OF SEQ ID NOS: 10

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      primer based on Bcl-2 gene

<400> SEQUENCE: 1
tgtccagtca gctgca                                                     16

<210> SEQ ID NO 2
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer based on Bcl-2 gene

<400> SEQUENCE: 2
tgaccccacc gaactca                                                    17

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on Bax gene

<400> SEQUENCE: 3
gggtggcagc tgacatgttt                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on Bax gene

<400> SEQUENCE: 4
cgctcacgga ggaagtccag                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on Bad gene

<400> SEQUENCE: 5
ctcgctggct cctgcacacg                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on Bad gene

<400> SEQUENCE: 6
gcgtcttcct gctcactcgg                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on Bak gene

<400> SEQUENCE: 7
gcttcagccc accgctggga                                                 20

<210> SEQ ID NO 8
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      primer based on Bak gene

<400> SEQUENCE: 8
cacgctggta gacatacagg                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer based on GAPDH gene

<400> SEQUENCE: 9
gtgaaggtcg gtgtgaacgg                                                   20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer based on GAPDH gene

<400> SEQUENCE: 10
gagtcatact ggaacatgta g                                                 21
```